United States Patent [19]

Corfield et al.

[11] 4,301,280
[45] Nov. 17, 1981

[54] PREPARATION OF 3-SUBSTITUTED CEPHALOSPORINS

[75] Inventors: John R. Corfield, Runcorn; Derek Johnson; Clifford G. Taylor, both of Warrington, all of England

[73] Assignee: Lilly Industries Limited, London, England

[21] Appl. No.: 145,531

[22] Filed: May 1, 1980

[30] Foreign Application Priority Data

May 8, 1979 [GB] United Kingdom ............... 15929/79

[51] Int. Cl.$^3$ .................. C07D 501/20; C07D 277/60
[52] U.S. Cl. .................................. 544/016; 548/153; 424/246; 544/111
[58] Field of Search ........................ 548/153; 424/246; 544/16

[56] References Cited
U.S. PATENT DOCUMENTS

| 4,079,181 | 3/1978 | Tsuji et al. | 544/133 |
| 4,160,085 | 7/1979 | Tsuji et al. | 544/133 |
| 4,226,986 | 10/1980 | Hatfield et al. | 548/153 |

Primary Examiner—Nicholas S. Rizzo
Attorney, Agent, or Firm—William B. Scanlon; Arthur R. Whale

[57] ABSTRACT

There is described a process for preparing an enamine of formula (IX):

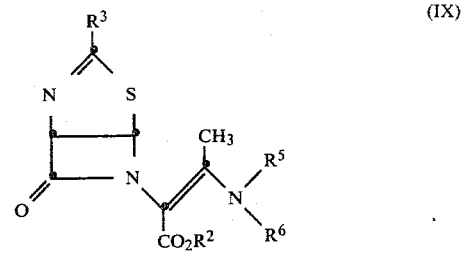

where $R^2$ is a carboxylic acid protecting group and $R^3$ is the residue of a carboxylic acid derived acyl group and where $R^5$ and $R^6$ are the same or different $C_{1-4}$ alkyl or $C_{7-10}$ aralkyl groups; or taken together with the adjacent nitrogen atom form a heterocyclic ring containing from 4 to 8 carbon atoms and optionally a further heteroatom selected from oxygen and nitrogen; by reacting a compound of formula (XII):

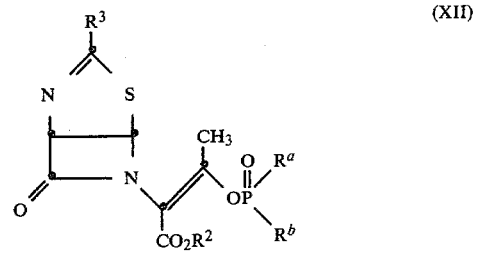

with an amine of formula $HNR^5R^6$, the reactant of formula (XII) being prepared by reaction of an appropriate enol derivative with a phosphorus reagent. The enamines of formula (IX) are useful in the preparation of 3-hydroxycephalosporins.

8 Claims, No Drawings

PREPARATION OF 3-SUBSTITUTED CEPHALOSPORINS

This invention relates to an improved process for preparing 3-substituted cephalosporin derivatives and embraces within its ambit novel intermediates useful in that process.

It has recently been discovered that 3-hydroxycephalosporins can be converted to their corresponding 3-alkoxy and 3-chloro derivatives and that those chloro and alkoxy derivatives are extremely efficacious antibacterial agents (see U.K. Patent Specifications Nos. 1,454,399 and 1,456,221 and U.S. Pat. No. 4,064,343).

Accordingly, a very great amount of research effort has been put into developing economically viable methods of preparing 3-hydroxycephalosporins. Perhaps, the best process heretofore described in the literature is that which appears in Example 17-III of U.S. Pat. No. 4,079,181 which process can be schematically illustrated by the following reaction schedule:

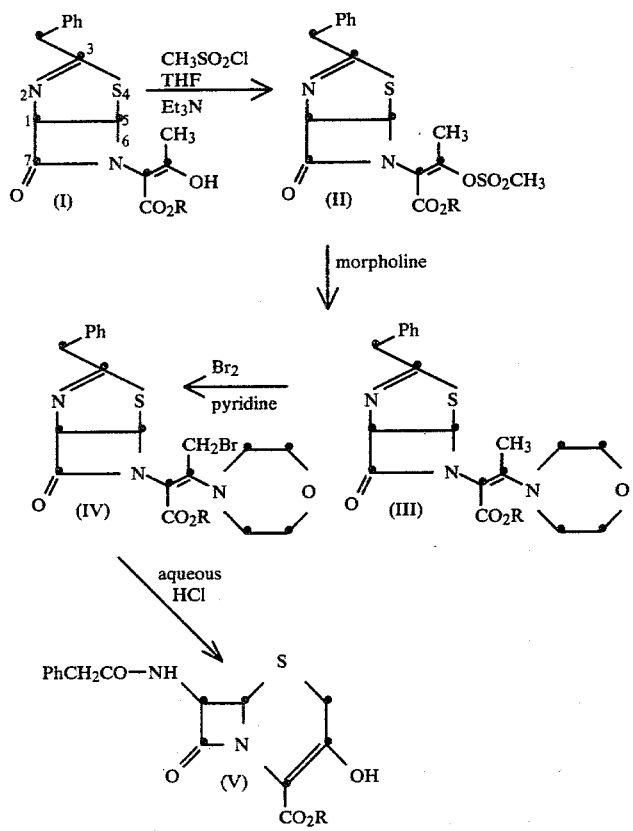

where R represents a para-nitrobenzyl ester protecting group.

It cannot be denied that this procedure constitutes an extremely valuable way of obtaining the 3-hydroxycephalosporin derivative (V). However, the Applicants have found that the yield of product (II) obtained in the functionalization of the enol (I) is considerably reduced (of the order of 10%) by formation of the C-mesylated product (VI):

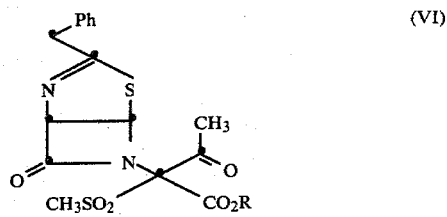

Thus, the maximum realizable yield of (V) is reduced by 10% and, of course, production of the unwanted C-mesylated product will result in purification problems during subsequent processing of the intermediate mixture ((II) and (VI)), as well as adversely affecting the stoichiometry of later reaction steps in the synthesis of the 3-hydroxycephem molecule (V).

The Applicants have found that, surprisingly, functionalisation of the enol (I) occurs exclusively at the oxygen atom if the methanesulphonyl chloride is replaced by a phosphorus reagent of formula (VII):

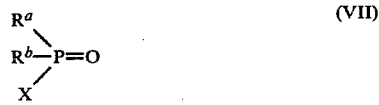

where
$R^a$ and $R^b$ are the same or different and can each represent phenyl or phenoxy optionally substituted by one to three groups selected from $C_{1-4}$ alkyl, $C_{1-4}$ alkoxy, halogen and nitro; or are $C_{1-4}$ alkyl, $C_{1-4}$ alkoxy, $C_{3-8}$ cycloalkyl, $C_{3-8}$ cycloalkoxy, chlorine or bromine;

X is chlorine, bromine, nitrile or azide; provided that:

(i) $R^a$ and $R^b$ cannot both be halogen; and (ii) when X is nitrile or azide, $R^a$ and $R^b$ are the same or different phenoxy; $C_{3-8}$ cycloalkoxy or $C_{1-4}$ alkoxy groups.

Preferably, the reagent of formula (VII) is that in which $R^a$ and $R^b$ are phenoxy optionally substituted by one to three groups selected from $C_{1-4}$ alkyl, $C_{1-4}$ alkoxy, halogen and nitro; $C_{1-4}$ alkoxy or $C_{3-8}$ cycloalkoxy and X is bromine or chlorine.

We have now discovered that, the product thus formed can be converted to the corresponding enamine derivative in high yield and under mild conditions. The enamine derivative can be converted to the corresponding 3-hydroxycephem of formula (V) using the reaction conditions described in U.S. Pat. No. 4,079,181.

Those skilled in the art will appreciate that in view of the extremely high cost involved in the preparation of cephalosporins, increases in yield of even a few percent can have a dramatic influence on the economics of production, and therefore commercial viability, of this kind of antibiotic.

The present invention provides a process for preparing a 3-hydroxy cephalosporin of formula (VIII):

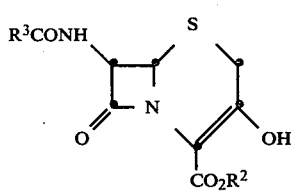
(VIII)

where $R^2$ is a carboxylic acid protecting group and $R^3$, together with the associated carbonyl group, is a carboxylic acid derived acyl group, which process comprises:

(a) halogenating a compound of formula (IX):

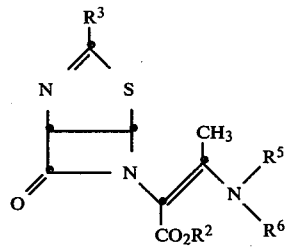
(IX)

where $R^5$ and $R^6$ are the same or different $C_{1-4}$ alkyl or $C_{7-10}$ aralkyl groups; or taken together with the adjacent nitrogen atom form a heterocyclic ring containing from 4 to 8 carbon atoms and optionally a further heteroatom selected from oxygen and nitrogen;

(b) cyclising the halo product (X):

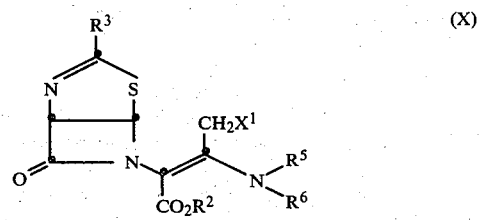
(X)

where $X^1$ is chlorine, bromine or iodine, of (a) into the 3-hydroxy cephalosporin of formula (VIII) wherein the compound of formula (IX) is prepared by (c) reacting an enol of formula (XI):

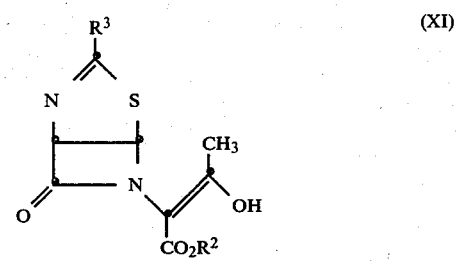
(XI)

with a phosphorus reagent of formula (VII):

(VII)

where $R^a$, $R^b$ and X are as previously defined, to form a product of formula (XII):

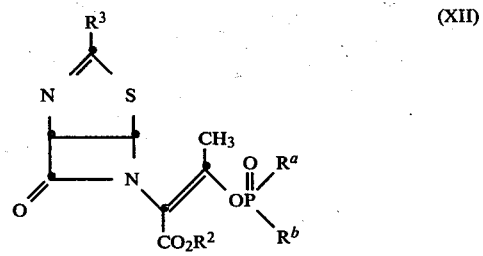
(XII)

followed by reaction of this product with an amine of formula $HNR^5R^6$ to form the amine starting material of formula (IX) utilized in step (a).

The reaction of the enol of formula (XI) with the phosphorus reagent of formula (VII) and the reaction of the product of formula (XII) with the amine of formula $HNR^5R^6$ are both novel and inventive and are therefore provided singly and in combination as further aspects of the invention.

For ease of representation, and to facilitate comprehension of the invention, structures possessing a side-chain double bond have been shown only in one of their stereoisomeric forms. However, those skilled in the art will immediately appreciate that these structures may exist in the alternative form and where this possibility exists, it is to be clearly understood that such alternative forms are embraced within the scope of the invention.

The carboxylic acid derived acyl group $R^3CO$ can be any of those groups conventionally utilized in the β-lactam art, the nature of which groups will be readily apparent to those skilled in this field. Thus, for instance the R³ residue may be:

(a) hydrogen, $C_{1-3}$ alkyl, halomethyl, cyanomethyl or 3(2-chlorophenyl)-5-methylisoxazol-4-yl;
(b) benzyloxy, 4-nitrobenzyloxy, 2,2,2-trichloroethoxy, tert-butoxy, or 4-methoxybenzyloxy;
(c) the group R" wherein R" is phenyl or phenyl substituted with 1 or 2 substituents independently selected from the group consisting of halo, protected hydroxy, nitro, cyano, trifluoromethyl, $C_{1-3}$ alkyl, and $C_{1-4}$ alkoxy;
(d) an arylalkyl group of the formula

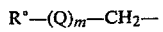

wherein R° is R" as defined above, 2-thienyl, 3-thienyl, or 1,4-cyclohexyldienyl, m is 0 or 1, and Q is O or S subject to the limitation that when m is 1 R° is R";
(e) a substituted arylalkyl group of the formula

wherein R° is as defined above and W is hydroxy, protected hydroxy, amino, protected amino, or protected carboxy; or
(f) a heteroarylmethyl group of the formula $R^4CH_2$- wherein $R^4$ is 2-furyl, 3-furyl, 2-thiazolyl, 5-isoxazolyl, or 5-tetrazolyl.

In the foregoing description the term "$C_{1-3}$ alkyl" refers to methyl, ethyl, n-propyl or isopropyl. Representative "$C_{1-4}$ alkoxy" groups are methoxy, ethoxy, n-propoxy, and tert-butoxy. "Halomethyl" represents chloromethyl, bromomethyl, fluoromethyl and iodomethyl.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a protected hydroxy phenyl group such as 4-benzyloxyphenyl, 3-benzyloxyphenyl, 4-tert-butoxyphenyl, 4-tetrahydropyranyloxyphenyl, 4-(4-nitrobenzyloxy)phenyl, 2-phenacyloxyphenyl, 4-benzhydroxyphenyl, 4-trityloxyphenyl and like groups; a nitrophenyl group such as 3-nitrophenyl or 4-nitrophenyl; a cyanophenyl group, for example, 4-cyanophenyl; a mono or dialkyl substituted phenyl group such as 4-methylphenyl, 2,4-dimethylphenyl, 2-ethylphenyl, 4-isopropylphenyl, 4-ethylphenyl, 3-n-propylphenyl and the like; a mono or dialkoxyphenyl group, for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R" represents disubstituted phenyl groups wherein the substituents are different for example, 3-methyl-4-methoxyphenyl, 3-chloro-4-benzyloxyphenyl, 2-methoxy-4-bromophenyl, 4-ethyl-2-methoxyphenyl, 3-chloro-4-nitrophenyl, 2-methyl-4-chlorophenyl and like disubstituted phenyl groups bearing different substituents.

The term "protected amino" as employed in the foregoing definition has reference to an amino group substituted with one of the commonly employed amino blocking groups such as the tert-butoxycarbonyl group; the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in "Protective Groups in Organic Chemistry" J. F. W. McOmie, Ed., Plenum Press, New York, N.Y., 1973, Chapter 2 shall be recognized as suitable.

The term "protected hydroxy" has reference to the readily cleavable groups formed with a hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

R³ is preferably benzyl or phenoxymethyl ($PhOCH_2$—).

The group $R^2$ is a carboxylic acid protecting group. This term refers to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_{2-6}$ alkanoyloxymethyl, 2-iodoethyl, p-nitrobenzyl, diphenylmethyl (benzhydryl), phenacyl, 4-halophenacyl, dimethylallyl, 2,2,2-trichloroethyl, tri($C_{1-3}$ alkyl)silyl, succinimidomethyl and like ester forming moieties. Other known carboxy protecting groups such as those described by E. Haslam in "Protective Groups in Organic Chemistry", supra, Chapter 5, shall be recognized as suitable. The nature of such ester forming groups is not critical although the Applicants have found that use of the para-nitrobenzyl protecting group is particularly desirable.

In the foregoing definitions, hydroxy, amino, and carboxy protecting groups are not exhaustively defined. The function of such groups is to protect the reactive functional groups, for example, during the preparation of the starting materials, and to then be removed at some later point in time without disrupting the remainder of the molecule. Many such protective groups are well known in the art and the use of other groups equally applicable to the process and compounds of the present invention shall be recognized as suitable. Thus, there is no novelty or inventiveness asserted with regard to the "protecting groups" referred to in this specification.

Representative of the acylamino group $R^3CONH$- in the compound of formula (VIII) are formamido, acetamido, propionamide, butyramido, 2-pentenoylamino, cyanoacetamido, chloroacetamido, bromoacetamido, 5-tert-butoxycarbonylamino, and 5-tert-butoxycarbonylvaleramido.

Illustrative of the particular acylamino group,

are benzamido, 2,6-dimethoxybenzamido, 4-chlorobenzamido, 4-methylbenzamido, 3,4-dichlorobenzamido, 4-cyanobenzamido, 3-bromobenzamido, and 3-nitrobenzamido.

Exemplary of the acylamino group

when $R^3$ is a group of the formula $R^o(Q)_mCH_2-$ and m is O, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido, 2-thienylacetamido, 3-thienylacetamido and the like; and when m is 1 and Q is O, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups; and when m is 1 and Q is S, representative groups are phenylthioacetamido, 2,5-dichlorophenylthioacetamido, 4-bromophenylthioacetamido, 4-methoxyphenylthioacetamido, 4-tolylthioacetamido and like substituted phenylthioacetamido groups.

Illustrative of the acylamino groups when $R^3$ is a substituted arylalkyl group of the formula $$R^o-\underset{W}{\underset{|}{CH}}-$$

and when W is protected hydroxy are 2-formyloxy-2-phenylacetamido, 2-benzyloxy-2-(4-methoxyphenyl)acetamido, 2-(4-nitrobenzyloxy)-2-(3-chlorophenyl)acetamido, 2-chloroacetoxy-2-(4-methoxyphenyl)acetamido, 2-benzyloxy-2-phenylacetamido, 2-trimethylsilyoxyl-2-(4-chlorophenyl)acetamido, and 2-benzhydryloxy-2-phenylacetamido. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)acetamido, 2-benzhydryloxycarbonylamino-2-phenylacetamido, 2-(1-carbomethoxy-2-propenyl-)amino-2-phenylacetamido and 2-(4-nitrobenzyloxycarbonylamino)-2-(2-thienyl)acetamido.

Exemplary of the acylamino group

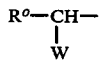

when $R^3$ is a heteroarylmethyl group of the formula $R^4-CH_2-$ are 2-furylacetamido, 3-furylacetamido, a 2-thiazolylacetamido group of the formula

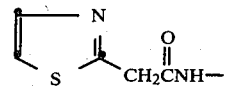

or a 5-isoxazolylacetamido group of the formula

The compound of formula (IX) may be halogenated using the reagents and conditions specified in U.S. Pat. No. 4,079,181. Suitable halogenating reagents include those which halogenate through the halogen cation or halogen radical or its equivalent. Representative halogenating reagents belong to the categories listed below:

1. $X_2^1$, BrCl, IBr, $C_6H_5I.X^1{}_2$, $C_5H_5N.HX^1.X_2^1$, $C_6H_5N(CH_3)_2.HX^1.X^1{}_2$, $(alkyl)_2SO_4.HX'$, $CuX_2{}'$.
2. $-OX^1$, $(alkyl)OX^1$, $HOX^1$, $(acyl)OX^1$.
3. $=NX^1$ $(alkyl)_4NX^1.X^1{}_2$, $NO_2X^1$, $(acyl)NHX^1$, $(acyl)_2NX^1$.
4. $-SX^1$, $SX^1{}_2$, $S+X^1{}_2$.
5. $-CX^1$, $X^1{}_2$, $CHOCH_3$, $CX^1{}_4$, α-haloketones, α-halosulfones, or like reagents, where alkyl and acyl contain up to 4 carbon atoms; and $X^1$ is chlorine, bromine or iodine. $X^1$ is preferably bromine.

When these halogenating reagents act via a halogen radical, the reaction can be initiated by heat, light, peroxide (peracid, peroxide, hydroperoxide, etc.), azo compound (azobisisobutyronitrile, etc.) or other radical initiator.

When these halogenating reagents act via a halogen cation, the reaction is preferably carried out in the presence of an acid-trapping reagent (organic or inorganic base, e.g. sodium carbonate, pyridine, quinoline, lutidine, morpholine, diethylamine, triethylamine etc.).

The reaction of the starting materials with the halogenating reagent is preferably carried out in an inert solvent. Suitable solvents include hydrocarbons (pentane, hexane, benzene, toluene, etc.), halogenated hydrocarbons (methylene chloride, chloroform, carbon tetrachloride, dichlorobenzene, etc.), esters (ethyl acetate, butyl acetate, methyl benzoate, etc.), ketones (acetone, cyclohexanone, benzophenone, etc.), ethers, (diethyl ether, ethyleneglycol dimethyl ether, tetrahydrofuran, tetrahydropyran, dioxan, anisole, etc.), alcohols (methanol, ethanol, ethyleneglycol, benzylalcohol, etc.), carboxylic acids (acetic acid, propionic acid, etc.), organic bases (butylamine, triethylamine, pyridine, picoline, etc.), organic amides (dimethylformamide, dimethylacetamide, hexamethylphosphorotriamide, etc.), organic nitriles (acetonitrile, benzonitrile, etc.), nitrohydrocarbons and alkyl sulfoxides (dimethyl sulfoxide, etc.).

Representative examples of suitable $-NR^5R^6$ groups are dimethylamino, diethylamino, methylethylamino, dipropylamino, dibutylamino, dibenzylamino and, when $R^5$ and $R^6$ represent a cyclic entity, morpholino, piperidino and piperazino. The preferred $-NR^5R^6$ group for use in the invention is morpholino.

The cyclisation reaction (b) can be effected by acid catalyzed hydrolysis. Suitable solvents for the cyclization are ethereal solvents e.g. tetrahydrofuran, tetrahydropyran and dioxan, amide solvents e.g. dimethylformamide, dimethylacetamide and hexamethylphosphorotriamide, halohydrocarbon solvents e.g. chloroform,

methylene chloride and dichloroethane, aliphatic and aromatic esters such as ethyl acetate, aliphatic ketones such as acetone, aliphatic and aromatic nitriles such as acetonitrile and alkyl sulphoxides such as dimethyl sulphoxide.

Suitable acids used to acidify the reaction medium include aqueous mineral acids (e.g. hydrochloric acid, hydrobromic acid, sulphuric acid, nitric acid, phosphoric acid, perchloric acid, sulphurous acid), aqueous aryl sulphonic acids such as p-toluene sulphonic acid and aqueous alkyl sulphonic acids such as methane sulphonic acid.

The reaction between the enol of formula (XI) and the phosphorus reagent of formula (VII) is preferably effected at a temperature in the range of from $-30°$ to $50°$ C., more preferably from $0°$ to $25°$ C. At these temperatures, reaction is substantially complete in from $\frac{1}{2}$ to 6 hours.

Any suitable inert organic solvent may be utilized. However, good results have been obtained using ethereal solvents such as diethyl ether, ethylene glycol dimethylether, tetrahydrofuran, tetrahydropyran, dioxan and anisole. The use of tetrahydrofuran as the ethereal solvent is preferred. In addition, excellent results have been obtained using as solvent haloalkanes such as methylene chloride, alkyl nitriles such as acetonitrile and aliphatic esters such as ethyl acetate.

The condensation reaction between the enol and the phosphorus compound proceeds with elimination of HX. The reaction is preferably effected in the presence of a base strong enough to generate the enolate anion such as a tertiary organic amine for example pyridine, triethylamine, N-methylmorpholine or quinoline.

In certain circumstances, it may be desirable to effect the condensation reaction in the presence of an acylation catalyst and in such a circumstance the catalyst utilized may be a 4-dialkylaminopyridine of the type described in *Angew. Chem. Int. Ed. Engl.* 17, 569–583 (1978).

Use of an inert gas atmosphere, such as nitrogen, is preferred.

Examples of suitable phosphorus compounds for use in the process of the invention are:
diphenylphosphoryl chloride,
diphenylphosphoryl bromide,
diethylphosphoryl chloride,
diethylphosphoryl bromide,
dibutylphosphoryl chloride,
dibutylphosphoryl bromide,
bis-(2-chlorophenyl)phosphoryl chloride,
bis-(3-chlorophenyl)phosphoryl bromide,
bis-(3-fluorophenyl)phosphoryl chloride,
bis-(4-iodophenyl)phosphoryl bromide,
bis-(2,3-dichlorophenyl)phosphoryl chloride,
bis-(3,4-dichlorophenyl)phosphoryl bromide,
bis-(4-methylphenyl)phosphoryl chloride,
bis-(4-butylphenyl)phosphoryl bromide,
bis-(3,4-dimethylphenyl)phosphoryl chloride,
bis-(3-chloro-4-methylphenyl)phosphoryl chloride,
bis-(3-methoxyphenyl)phosphoryl chloride,
bis-(4-methoxyphenyl)phosphoryl chloride,
bis-(3-butoxyphenyl)phosphoryl chloride,
bis-(4-nitrophenyl)phosphoryl chloride,
bis-(3,4,5-trimethoxyphenyl)phosphoryl chloride,
bis-(3,4,5-trimethoxyphenyl)phosphoryl bromide,
bis-(2-methoxy-3-methyl-4-fluorophenyl)phosphoryl chloride,
dicyclopropylphosphoryl chloride,
dicyclopropylphosphoryl bromide,
dicyclohexylphosphoryl chloride,
dicyclohexylphosphoryl bromide,
dicyclooctylphosphoryl chloride,
dicyclooctylphosphoryl bromide,
dimethylphosphoryl azide,
dimethylphosphoryl cyanide,
diethylphosphoryl azide,
diethylphosphoryl cyanide,
diphenylphosphoryl azide
diphenylphosphoryl cyanide,
dicyclohexylphosphoryl azide,
dicyclohexylphosphoryl cyanide,
methyl phosphorodichloridate,
methyl phosphorodibromidate,
ethyl phosphorodichloridate,
ethyl phosphorodibromidate,
propyl phosphorodichloridate,
isopropyl phosphorodichloridate,
butyl phosphorodichloridate,
phenyl phosphorodichloridate,
phenyl phosphorodibromidate,
2-chlorophenyl phosphorodichloridate,
2-chlorophenyl phosphorodibromidate,
3-chlorophenyl phosphorodichloridate,
3-fluorophenyl phosphorodichloridate,
2,4-dichlorophenyl phosphorodichloridate,
2,4-dichlorophenyl phosphorodibromidate,
3,4-dichlorophenyl phosphorodichloridate,
4-methylphenyl phosphorodichloridate,
3-chloro-4-methylphenyl phosphorodichloridate,
3-methoxyphenyl phosphorodichloridate,
4-methoxyphenyl phosphorodichloridate,
3-butoxyphenyl phosphorodichloridate,
4-nitrophenyl phosphorodichloridate,
3,4,5-trimethoxyphenyl phosphorodichloridate,
cyclopropyl phosphorodichloridate,
cyclopentyl phosphorodichloridate,
cyclohexyl phosphorodichloridate,
cyclohexyl phosphorodibromidate,
cyclooctyl phosphorodichloridate,
methyl methylphosphonochloridate,
methyl methylphosphonobromidate,
methyl phenylphosphonochloridate,
ethyl methylphosphonochloridate,
ethyl ethylphosphonochloridate,
ethyl ethylphosphonobromidate,
ethyl phenylphosphonochloridate,
ethyl 3-chlorophenylphosphonochloridate,
ethyl 2,4-dichlorophenylphosphonochloridate,
ethyl 4-methylphenylphosphonochloridate,
ethyl 4-methoxyphenylphosphonochloridate,
ethyl 4-nitrophenylphosphonochloridate,
ethyl cyclopentylphosphonochloridate,
phenyl methylphosphonochloridate,
phenyl phenylphosphonochloridate,
phenyl phenylphosphonobromidate,
phenyl 4-methylphenylphosphonochloridate,
phenyl cyclohexylphosphonochloridate,
2,4-dichlorophenyl ethylphosphonochloridate,
2,4-dichlorophenyl phenylphosphonochloridate,
2,4-dichlorophenyl cyclohexylphosphonochloridate,
4-nitrophenyl ethylphosphonochloridate,
4-nitrophenyl phenylphosphonochloridate,
4-nitrophenyl cyclohexylphosphonochloridate,
3,4,5-trimethoxyphenyl ethylphosphonochloridate,
3,4,5-trimethoxyphenyl phenylphosphonochloridate,
cyclopentyl ethylphosphonochloridate, cyclopentyl phenylphosphonochloridate,
cyclohexyl phenylphosphonochloridate,
dimethylphosphinyl chloride,
dimethylphosphinyl bromide,
diethylphosphinyl chloride,
diethylphosphinyl bromide,
dipropylphosphinyl chloride,
di-isopropylphosphinyl chloride,
dibutylphosphinyl chloride,
diphenylphosphinyl chloride,
diphenylphosphinyl bromide,
bis-(2-chlorophenyl)phosphinyl chloride,
bis-(2-chlorophenyl)phosphinyl bromide,
bis-(3-chlorophenyl)phosphinyl chloride,
bis-(3-fluorophenyl)phosphinyl chloride,
bis-(2,4-dichlorophenyl)phosphinyl chloride,
bis-(3,4-dichlorophenyl)phosphinyl chloride,
bis-(4-methylphenyl)phosphinyl chloride,
bis-(3-chloro-4-methylphenyl)phosphinyl chloride,
bis-(3-methoxyphenyl)phosphinyl chloride,
bis-(4-methoxyphenyl)phosphinyl chloride,
bis-(3-butoxyphenyl)phosphinyl chloride,
bis-(4-nitrophenyl)phosphinyl chloride,
bis-(3,4,5-trimethoxyphenyl)phosphinyl chloride,
dicyclopropylphosphinyl chloride,
dicyclopentylphosphinyl chloride,
dicyclohexylphosphinyl chloride,
dicyclohexylphosphinyl bromide, and
dicyclooctylphosphinyl chloride.

Use of diphenylphosphoryl chloride as the phosphorus reagent is preferred.

The product of the condensation reaction is a compound of formula (XII). Such compounds are novel and are provided in a further aspect of the invention. Representative examples of these novel intermediates are listed below:

dimethyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
diethyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
diisopropyl 1-(3-phenoxymethyl-7-oxo-4-thia-2,6-diazabicyclo[3,2-0]hept-2-en-6-yl)-1-(p-nitrobenzyloxycarbonyl)-prop-1-en-2-yl phosphate,
dicyclopentyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
dicyclohexyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
diphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-2-chlorophenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-3,4-dichlorophenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-4-methylphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-3-methoxyphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-3,4,5-trimethoxyphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
bis-4-nitrophenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate,
dimethyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate,
diethyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate,
dicyclopentyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate,
diphenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate,
bis-4-methoxyphenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate,
diethyl 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl phosphate,
diphenyl 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl phosphate,
diethyl 1-(3-benzyl-7-oxo-4-thia-2,6-diazabicyclo[3,2,0]hept-2-en-6-yl)-1-(2,2,2-trichloroethoxycarbonyl)-prop-1-en-2-yl phosphate,
diphenyl 1-(3-benzyl-7-oxo-4-thia-2,6-diazabicyclo[3,2,0]hept-2-en-6-yl)-1-(2,2,2-trichloroethoxycarbonyl)-prop-1-en-2-yl phosphate,
diethyl 1-(3-phenoxymethyl-7-oxo-4-thia-2,6-diazabicyclo[3,2,0]hept-2-en-6-yl)-1-(diphenylmethoxycarbonyl)-prop-1-en-2-yl phosphate,
diphenyl 1-(3-phenoxymethyl-7-oxo-4-thia-2,6-diazabicyclo[3,2,0]hept-2-en-6-yl)-1-(diphenylmethoxycarbonyl)-prop-1-en-2-yl phosphate,
diethyl 1-(3-benzyl-7-oxo-4-thia-2,6-diazabicyclo[3,2,0]hept-2-en-6-yl)-1-(diphenylmethoxycarbonyl)-prop-1-en-2-yl phosphate,
diphenyl 1-(3-benzyl-7-oxo-4-thia-2,6-diazabicyclo[3,2,0]hept-2-en-6-yl)-1-(diphenylmethoxycarbonyl)-prop-1-en-2-yl phosphate,
diethyl 1-(3-phenoxymethyl-7-oxo-4-thia-2,6-diazabicyclo[3,2,0]hept-2-en-6-yl)-1-(benzyloxycarbonyl)-prop-1-en-2-yl phosphate,
diphenyl 1-(3-phenoxymethyl-7-oxo-4-thia-2,6-diazabicyclo[3,2,0]hept-2-en-6-yl)-1-(benzyloxycarbonyl)-prop-1-en-2-yl phosphate,
diethyl 1-(3-benzyl-7-oxo-4-thia-2,6-diazabicyclo[3,2,0]hept-2-en-6-yl)-1-(benzyloxycarbonyl)-prop-1-en-2-yl phosphate,
diphenyl 1-(3-benzyl-7-oxo-4-thia-2,6-diazabicyclo[3,2,0]hept-2-en-6-yl)-1-(benzyloxycarbonyl)-prop-1-en-2-yl phosphate,
diethyl 1-(3-phenoxymethyl-7-oxo-4-thia-2,6-diazabicyclo[3,2,0]hept-2-en-6-yl)-1-(t-butoxycarbonyl)-prop-1-en-2yl phosphate,
diphenyl 1-(3-phenoxymethyl-7-oxo-4-thia-2,6-diazabicyclo[3,2,0]hept-2-en-6-yl)-1-(t-butoxycarbonyl)-prop-1-en-2-yl phosphate,
diethyl 1-(3-benzyl-7-oxo-4-thia-2,6-diazabicyclo[3,2,0]hept-2-en-6-yl)-1-(t-butoxycarbonyl)-prop-1-en-2-yl phosphate, diphenyl 1-(3-benzyl-7-oxo-4-thia-2,6-diazabicyclo[3,2,0]hept-2-en-6-yl)-1-(t-butoxycarbonyl)-prop-1-en-2-yl phosphate, diethyl 1-(3-phenoxymethyl-7-oxo-4-thia-2,6-diazabicyclo[3,2,0]hept-2-en-6-yl)-1-(p-methoxyoxycarbonyl)-prop-1-en-2-yl phosphate, diphenyl 1-(3-phenoxymethyl-7-oxo-4-thia-2,6-diazabicyclo[3,2,0]hept-2-en-6-yl)-1-(p-methoxybenzyloxycarbonyl)-prop-1-en-2-yl phosphate, diethyl 1-(3-benzyl-7-oxo-4-thia-2,6-diazabicyclo[3,2,0]hept-2-en-6-yl)-1-(p-methoxybenzyloxycarbonyl)-prop-1-en-2-yl phosphate, diphenyl 1-(3-benzyl-7-oxo-4-thia-2,6-diazabicyclo[3,2,0]hept-2-en-6-yl)-1-(p-methoxybenzyloxycarbonyl)-prop-1-en-2-yl phosphate, methyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, methyl-1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorobromidate, ethyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, isopropyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, cyclopentyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, cyclohexyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, phenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, phenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorobromidate, 2-chlorophenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, 4-methylphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, 4-methoxyphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphorochloridate, ethyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphorochloridate, phenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphorochloridate, 4-methoxyphenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphorochloridate, ethyl 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl phosphorochloridate, phenyl 1-(3-benzyl-7-oxo-4-thia-2,6-diazabicyclo[3,2,0]hept-2-en-6-yl)-1-(2,2,2-trichloroethoxycarbonyl)-prop-1-en-2-yl phosphorochloridate, ethyl 1-(3-benzyl-7-oxo-4-thia-2,6-diazabicyclo[3,2,0]hept-2-en-6-yl)-1-(diphenylmethoxycarbonyl)-prop-1-en-2-yl phosphorochloridate, phenyl 1-(phenoxymethyl-7-oxo-4thia-2,6-diazabicyclo[3,2,0]hept-2-en-6-yl)-1-(diphenylmethoxycarbonyl)-prop-1-en-2-yl phosphorochloridate, ethyl 1-(3-phenoxymethyl-7-oxo-4-thia-2,6-diazabicyclo[3,2,0]hept-2-en-6-yl)-1-(benzyloxycarbonyl)-prop-1-en-2-yl phosphorochloridate, phenyl 1-(3-benzyl-7-oxo-4-thia-2,6-diazabicyclo[3,2,0] hept-2-en-6-yl)-1-(benzyloxycarbonyl)-prop-1-en-2-yl phosphorochloridate, ethyl 1-(3-benzyl-7-oxo-4-thia-2,6-diazabicyclo[3,2,0]hept-2-en-6-yl)-1-(t-butoxycarbonyl)-prop-1-en-2-yl phosphorochloridate, phenyl 1-(3-phenoxymethyl-7-oxo-4-thia-2,6-diazabicyclo[3,2,0]hept-2-en-6-yl)-1-(t-butoxycarbonyl)-prop-1-en-2-yl phosphorochloridate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl dimethylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl diethylphosphinate, 1-(3-phenoxymethyl-7-oxo-4-thia-2,6-diazabicyclo[3,2,0]hept-2-en-6)-1-(p-nitrobenzyloxycarbonyl)-prop-1-en-2-yl dicyclohexylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl diphenylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl bis-2-chlorophenylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl bis-2,4-dichlorophenylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl bis-4-methylphenylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl bis-3-methoxyphenylphosphinate, 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl bis-4-nitrophenylphosphinate, 1-(3-benzyl-7-oxo-4-thia-2,6-diazabicyclo[3,2,0]hept-2-en-6-yl)-1-(p-nitrobenzyloxycarbonyl)prop-1-en-2-yl dimethylphosphinate, 1-(3-benzyl-7-oxo-4-thia-2,6-diazabicyclo[3,2,0]hept-2-en-6-yl)-1-(p-nitrobenzyloxycarbonyl)prop-1-en-2yl bis-4-methoxyphenylphosphinate, 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl diethylphosphinate, 1-(3-benzyl-7-oxo-4-thia-2,6-diazabicyclo[3,2,0]hept-2-en-6-yl)-1-(2,2,2-trichloroethoxycarbonyl)-prop-1-en-2-yl diethylphosphinate, 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl diphenylphosphinate, 1-(3-benzyl-7-oxo-4-thia-2,6-diazabicyclo[3,2,0]-hept-2-en-6-yl)-1-(2,2,2-trichloroethoxycarbonyl)-prop-1-en-2-yl diphenylphosphinate,
1-(3-phenoxymethyl-7-oxo-4-thia-2,6-diazabicyclo[3,2,0]hept-2-en-6-yl)-1-(benzyloxycarbonyl)-prop-1-en-2-yl diethylphosphinate,
1-(3-benzyl-7-oxo-4-thia-2,6-diazabicyclo[3,2,0]-hept-2-en-6-yl)-1-(benzyloxycarbonyl) prop-1-en-2-yl diphenylphosphinate,
1-(3-phenoxymethyl-7-oxo-4-thia-2,6-diazabicyclo[3,2,0]hept-2-en-6-yl)-1-diphenylmethoxycarbonyl)-prop-1-en-2-yl diethylphosphinate,
1-(3-benzyl-7-oxo-4-thia-2,6-diazabicyclo[3,2,0]hept-2-en-6-yl)-1-(p-nitrobenzyloxycarbonyl)-prop-1-en-2yl bis-4-methoxyphenylphosphinate,
1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl diethylphosphinate,
1-(3-benzyl-7-oxo-4-thia-2,6-diazabicyclo[3,2,0]hept-2-en-6-yl) 1-(2,2,2-trichloroethoxycarbonyl)-prop-1-en-2-yl diethylphosphinate,
1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl diphenylphosphinate,
1-(3-benzyl-7-oxo-4-thia-2,6-diazabicyclo[3,2,0]hept-2-en-6-yl)-1-(2,2,2-trichloroethoxycarbonyl)-prop-1-en-2-yl diphenylphosphinate,
1-(3-phenoxymethyl-7-oxo-4-thia-2,6-diazabicyclo[3,2,0]hept-2-en-6-yl)-1-(benzyloxycarbonyl)-prop-1-en-2-yl diethylphosphinate,
1-(3-benzyl-7-oxo-4-thia-2,6-diazabicyclo[3,2,0]hept-2-en-6-yl)-1-(benzyloxycarbonyl) prop-1-en-2-yl diphenylphosphinate,
1-(3-phenoxymethyl-7-oxo-4-thia-2,6-diazabicyclo[3,2,0]hept-2-en-6-yl)-1-diphenylmethoxycarbonyl)-prop-1-en-2-yl diethylphosphinate,
1-(3-benzyl-7-oxo-4-thia-2,6-diazabicyclo[3,2,0]hept-2-en-6-yl)-1-(diphenylmethoxycarbonyl)-prop-1-en-2-yl diphenylphosphinate,
methyl 1-(3-benzyl-7-oxo-4-thia-2,6-diazabicyclo[3,2,0]hept-2-en-6-yl)-1-(p-nitrobenzyloxycarbonyl)-prop-1-en-2-yl phenylphosphonate,
ethyl 1-(3-benzyl-7-oxo-4-thia-2,6-diazabicyclo[3,2,0]hept-2-en-6-yl)-1-(p-nitrobenzyloxycarbonyl)-prop-1-en-2-yl ethylphosphonate,
phenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phenylphosphonate,
ethyl 1-(3-phenoxymethoxy-7-oxo-4-thia-2,6-diazabicyclo[3,2,0]hept-2-en-6-yl)-1-(2,2,2-trichloroethoxycarbonyl)-prop-1-en-2-yl ethylphosphonate,
phenyl 1-(3-benzyl-7-oxo-4-thia-2,6-diazabicyclo[3,2,0]hept-2-en-6-yl)-1-(2,2,2-trichloroethoxycarbonyl)-prop-1-en-2-yl phenylphosphonate,
ethyl 1-(3-benzyl-7-oxo-4-thia-2,6-diazabicyclo[3,2,0]hept-2-en-6-yl)-1-(2,2,2-trichloroethoxycarbonyl)-prop-1-en-2-yl ethylphosphonate,
phenyl 1-(3-phenoxymethyl-7-oxo-4-thia-2,6-diazabicyclo[3,2,0]hept-2-en-6-yl)-1-(2,2,2-trichloroethoxycarbonyl)-prop-1-en-2-yl phenylphosphonate,
ethyl 1-(3-phenoxymethyl-7-oxo-4-thia-2,6-diazabicyclo[3,2,0]hept-2-en-6-yl)-1-(benzyloxycarbonyl)-prop-1-en-2-yl ethylphosphonate,
phenyl 1-(3-benzyl-7-oxo-4-thia-2,6-diazabicyclo[3,2,0]hept-2-en-6-yl)-1-benzyloxycarbonyl)-prop-1-en-2-yl phenylphosphonate,
ethyl 1-(3-phenoxymethyl-7-oxo-4-thia-2,6-diazabicyclo[3,2,0]hept-2-en-6-yl)-1-(diphenylmethoxycarbonyl)-prop-1-en-2-yl ethylphosphonate, and
phenyl 1-(3-benzyl-7-oxo-4-thia-2,6-diazabicyclo[3,2,0]hept-2-en-6-yl)-1-(diphenylmethoxycarbonyl)-prop-1-en-2-yl phenylphosphonate.

Conversion of the intermediate of formula (XII) to the amine starting material of formula (IX) is preferably effected at a temperature in the range of from −10° to 50° C., most preferably from 0° to 5° C. Any suitable organic solvent may be utilized for the conversion, especially those mentioned previously in connection with the reaction of the enol of formula (XI) and the phosphorus reagent of formula (VII). The amine $HNR^5R^6$, where $R^5$ and $R^6$ are as previously defined, should be used in the form of the free base.

A very great advantage of the process of the invention is that since reaction conditions, temperature, solvent, etc., are very similar for each of the reaction stages, the whole procedure can be carried out in "one pot".

To further illustrate the invention and to show how the same may be carried into effect reference will now be made to the following non-limitative Examples.

EXAMPLE 1 p-Nitrobenzyl 7-phenylacetamido-3-hydroxy-3-cephem-4-carboxylate

To a stirred suspension of p-nitrobenzyl α-[3-benzyl-7-oxo-4-thia-2,6-diazabicyclo[3,2,0]-hept-2-en-6-yl]-α-(1-hydroxyethylidene)acetate (9.06 g) in tetrahydrofuran (120 ml) under a nitrogen atmosphere at 20° C. was added triethylamine (3.21 ml) and diphenylphosphoryl chloride (4.77 ml). The reaction was stirred for 2 hours and then cooled to 0° C. Morpholine (4.01 ml) was added and the reaction stirred for 2 hours at 0°–5° C. The reaction was then cooled to −30° to −35° C. and pyridine (1.62 ml) added, followed by bromine (1.00 ml) dropwise over a period of 10 minutes.

The reaction was stirred for 20 minutes at −30° to −35° C., and then 5% hydrochloric acid (144 ml), methanol (120 ml) and tetrahydrofuran (20 ml) added. The reaction was then stirred at room temperature for 3 hours and stood at 0° C. overnight. The product was isolated by filtration, and washed with methanol (30 ml), water (30 ml) and methanol (30 ml) and then dried in vacuo at 40° C. for 5 hours. The total yield of title compound was 8.05 g (86%).

EXAMPLE 2 p-Nitrobenzyl 7-phenoxyacetamido-3-hydroxy-3-cephem-4-carboxylate

To a stirred solution of p-nitrobenzyl α-[3-phenoxymethyl-7-oxo-4-thia-2,6-diazabicyclo [3,2,0]hept-2-en-6-yl]-α-(1-hydroxyethylidene)acetate (9.38 g) in tetrahydrofuran (120 ml) under a nitrogen atmosphere at 20° C. was added triethylamine (3.21 ml) followed by diphenylphosphoryl chloride (4.77 ml). The reaction mixture was then stirred for 2 hours and cooled to 0° C. Morpholine (4.01 ml) was added and the reaction mixture stirred for 2 hours at 0°–5° C. The reaction mixture was next cooled to −30° to −35° C. and pyridine (1.62 ml) added followed by the dropwise addition of bromine (1.00 ml) over a period of 10 minutes. The reaction mixture was stirred at −30° to −35° C. for 20 minutes and 5% hydrochloric acid (144 ml) added, followed by further stirring at room temperature for 3 hours. The reaction mixture was then stood at 0° C. overnight. The reaction mixture was extracted with dichloromethane and the organic extracts washed with water then saturated sodium chloride solution, dried with magnesium sulphate and evaporated to dryness. The product thus obtained was dissolved in dichloromethane and acetic acid added, the dichloromethane removed under reduced pressure and then ether was added with stirring to complete crystallization. The product was isolated by filtration, washed with ether then dried in vacuo at 40° C. for 5 hours. The yield of p-nitrobenzyl 7-phenoxyacetamido-3-hydroxy-3-cephem-4-carboxylate acetic acid solvate was 9.16 g (84%).

EXAMPLE 3

Diethyl 1-(3-benzyl-7-oxo-4-thia-2,6-diazabicyclo [3,2,0]hept-2-en-6-yl)-1-(p-nitrobenzyloxycarbonyl)-prop-1-en-2-yl phosphate To a solution of p-nitrobenzyl α-(3-benzyl-7-oxo-4-thia-2,6-diazabicyclo[3,2,0]hept-2-en-6-yl)-α-(1-hydroxyethylidene)acetate (4.53 g) containing 4-dimethylaminopyridine (0.1 g) in ethyl acetate (50 ml) under a nitrogen atmosphere at 20° C. was added triethylamine (1.53 ml) followed by diethylphosphoryl chloride (1.59 ml) dropwise. The reaction mixture was stirred at 20° C. for 3 hours. Water (40 ml) was added and the organic layer was separated, washed with water (20 ml) and saturated sodium chloride solution (20 ml), dried with magnesium sulphate and carbon treated, filtered and evaporated to give the title compound as a yellow viscous oil in essentially quantitative yield. TLC (silica) $R_f$ 0.17 (dichloromethane/ethyl acetate 15:2). The product was a mixture of geometric isomers (ca. 2:1) about the enol phosphate double bond. NMR $\delta$CDCl$_3$ 1.11–1.60 (m, 6H), 1.98+2.60 (d, 3H), 3.73–4.65 (m, 6H), 5.22–5.42 (m, 2H), 5.88–6.28 (m, 2H) and 7.25–7.80 and 8.18–8.58 (m, 9H).

EXAMPLE 4

Diphenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate To a suspension of p-nitrobenzyl α-(3-benzyl-7-oxo-4-thia-2,6-diazabicyclo[3,2,0]-hept-2-en-6-yl)-α-(1-hydroxyethylidene) acetate (4.53 g) in tetrahydrofuran (60 ml) under a nitrogen atmosphere at 20° C. was added triethylamine (1.53 ml) followed by diphenylphosphoryl chloride (2.28 ml) dropwise. The reaction mixture was stirred at 20° C. for 2 hours. Water (50 ml) was then added and the mixture was extracted with dichloromethane (60 ml). The organic layer was separated, washed with water (30 ml) and saturated sodium chloride solution (30 ml), dried with magnesium sulphate, filtered and evaporated to give the title compound as a yellow viscous oil in essentially quantitative yield. TLC (silica) $R_f$ 0.68 (dichloromethane/ethyl acetate 15:2). The product was a mixture of geometric isomers (ca. 4:1) about the enol phosphate double bond. NMR$\delta$CDCl$_3$ 1.93 (d, J=2 Hz)+2.58 (d, J=2 Hz) (3H), 3.48–3.90 (m, 2H), 5.05 (s, 2H), 5.5–6.0 (m, 2H) and 7.0–8.2 (m, 19H).

EXAMPLE 5

Diphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate To a solution of p-nitrobenzyl α-(3-phenoxymethyl-7-oxo-4-thia-2,6-diazabicyclo[3,2,0]-hept-2-en-6-yl)-α-(1-hydroxyethylidene) acetate (9.38 g) in dichloromethane (100 ml) under a nitrogen atmosphere at 20° C. was added triethylamine followed by diphenylphosphoryl chloride (4.35 ml). The reaction mixture was stirred at 20° C. for 2 hours. Water (50 ml) was added and the organic layer was separated, washed with water (40 ml) and saturated sodium chloride solution (40 ml), dried with magnesium sulphate, filtered and evaporated to give the title compound as a yellow viscous oil in essentially quantitative yield. TLC (silica) $R_f$ 0.060 (ethyl acetate). The product was a mixture of geometric isomers (ca. 3:1) about the enol phosphate double bond. TLC separation of these isomers could be achieved; $R_f$ 0.52 and 0.45 (toluene/ethyl acetate, 1/1). NMR$\delta$CDCl$_3$ 2.10 (d, J=2 Hz)+2.63 (d, J=2 Hz) (3H), 4.22 and 4.67 (ABq, J=14 Hz, 2H), 5.11 (s, 2H), 5.50–5.77 (m, 2H) and 6.50–8.13 (m, 19H).

EXAMPLE 6 p-Nitrobenzyl α-(3-benzyl-7-oxo-4-thia-2,6-diazabicyclo[3,2,0]hept-2-en-6-yl)-α-(1-morpholinoethylidene) acetate To a solution of diethyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate (5.90 g) in dichloromethane (70 ml) at 0°–5° C. was added morpholine (1.83 ml) dropwise and the reaction mixture stirred at this temperature for 2 hours. Water (40 ml) was added and the organic layer was separated, washed with water (30 ml) and saturated sodium chloride solution (30 ml), dried with magnesium sulphate, filtered and evaporated to give the title compound as a yellow foam in almost quantitative yield. TLC (silica) $R_f$ 0.60 (ethyl acetate). The product was a mixture of geometric isomers (ca. 1:1.4) about the enamine double bond. NMR$\delta$CDCl$_3$ 1.72+2.40 (s, 3H), 3.01–4.07 (m, 10H), 5.22 (s, 2H), 5.60–6.13 (m, 2H), 7.28–7.77 and 8.10–8.40 (m, 9H).

EXAMPLE 7 p-Nitrobenzyl α-(3-benzyl-7-oxo-4-thia-2,6-diazabicyclo[3,2,0]hept-2-en-6-yl)-α-(1-morpholinoethylidene)acetate To a solution of diphenyl 1-(3-benzyl-7-oxo-4-thia-2,6-diazabicyclo[3,2,0]hept-2-en-6-yl)-1-(p-nitrobenzyloxycarbonyl)-prop-1-en-2-yl phosphate (6.86 g) in acetonitrile (50 ml) at 0°–5° C. was added morpholine (1.83 ml) dropwise and the reaction mixture stirred at this temperature for 2 hours. Water (50 ml) was added and the mixture was extracted with ethyl acetate (40 ml). The organic layer was separated, washed with water (30 ml) and saturated sodium chloride solution (30 ml), dried with magnesium sulphate, filtered and evaporated to give the title compound as a yellow foam in almost quantitative yield. The product obtained was a mixture of geometric isomers (ca. 1:1.4) about the enamine double bond and was identical to that produced in Example 6.

EXAMPLE 8 p-Nitrobenzyl α-(3-phenoxymethyl-7-oxo-4-thia-2,6-diazabicyclo[3,2,0]hept-2-en-6-yl)-α-(1-morpholinoethylidene)acetate To a solution of diphenyl 1-(3-phenoxymethyl-7-oxo-4-thia-2,6-diazabicyclo[3,2,0]hept-2-en-6-yl)-1-(p-nitrobenzyloxycarbonyl)-prop-1-en-2-yl phosphate (7.02 g) in ethyl acetate (70 ml) at 0°–5° C. was added morpholine (1.83 ml) dropwise and the reaction mixture stirred at this temperature for 2 hours. Water (30 ml) was added and the organic layer was separated, washed with water (30 ml) and saturated sodium chloride solution (30 ml), dried with magnesium sulphate, filtered and evaporated to give the title compound as a yellow foam in almost quantitative yield. TLC (silica) $R_f$ 0.57 (ethyl acetate). The product was a mixture of geometric isomers (ca. 1:1.4) about the enamine double bond. NMR δ CDCl$_3$ 1.93 (s), +2.43 (s) (3H), 3.17–3.93 (m, 8H), 4.90 (s, 2H), 5.25 (s, 2H), 5.68–6.13 (m, 2H) and 6.87–7.7+8.1–8.4 (m, 9H).

EXAMPLE 9

1-(3-Phenoxymethyl-7-oxo-4-thia-2,6-diazabicyclo(3,2,0)hept-2-en-6-yl)-1-(p-nitrobenzyloxycarbonyl)-prop-1-en-2-yl diphenylphosphinate To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (4.69 g) in tetrahydrofuran (60 ml) under a nitrogen atmosphere at 0°–5° C. was added triethylamine (1.6 ml.) followed by diphenylphosphinyl chloride (2.73 g.) dropwise over 5 minutes. After stirring for 3 hours at 20° C., the tetrahydrofuran was evaporated and the residue dissolved in dichloromethane. The resulting solution was washed with 1% hydrochloric acid and then water, dried with magnesium sulphate and evaporated to give the title compound as a pale yellow friable foam in essentially quantitative yield. TLC (silica) $R_F$ 0.54 (ethyl acetate). NMRδCDCl$_3$ 2.5 (s, 3H), 3.63 and 4.40 (ABq, 2H, J=14 Hz), 5.13 (s, 2H), 5.68 (d, 1H, J=4 Hz), 5.85 (d, 1H, J=4 Hz) and 6.5–8.03 (m, 20H).

EXAMPLE 10

Phenyl 1-(3-phenoxymethyl-7-oxo-4-thia-2,6-diazabicyclo(3,2,0)hept-2-en-6-yl)-1-(p-nitrobenzyloxycarbonyl)-prop-1-en-2-yl phenylphosphonate To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (4.69 g) in tetrahydrofuran (60 ml.) under a nitrogen atmosphere at 0° C. was added triethylamine (1.6 ml.) followed by phenyl phenylphosphonochloridate (2.91 g). After stirring for 3 hours at 20° C., the tetrahydrofuran was evaporated and the residue dissolved in dichloromethane. The resulting solution was washed with 1% hydrochloric acid and then water, dried with magnesium sulphate and evapoated to give the title compound as a pale yellow friable foam in essentially quantitative yield. TLC (silica)$R_f$ 0.64 (ethyl acetate). NMR δCDCl$_3$ 2.60 (m, 3H), 3.70–4.67 (m, 2H), 5.15 (s, 2H), 5.57–5.87 (m, 2H) and 6.6–8.17 (m, 19H).

EXAMPLE 11

Diphenyl 1-(3-benzyl-7-oxo-4-thia-2,6-diazabicyclo(3,2,0)hept-2-en-6-yl)-1-(diphenylmethoxycarbonyl)-prop-1-en-2-yl phosphate To a stirred solution of benzhydryl α-(3-benzyl-7-oxo-4-thia-2,6-diazabicyclo(3,2,0)hept-2-en-6-yl)-α-(1-hydroxyethylidene)acetate (2.42 g.) in tetrahydrofuran (30 ml.) under a nitrogen atmosphere at 20° C. was added triethylamine (0.74 ml.) followed by diphenylphosphoryl chloride (1.09 ml.). After stirring for 2 hours at 20° C., the reaction mixture was diluted with dichloromethane, washed with brine, dried with magnesium sulphate and evaporated to give the title compound as a pale yellow foam in essentially quantitative yield. TLC (silica) $R_f$ 0.58 (ethyl acetate). NMR δ CDCl$_3$ 2.57 (d, 3H, J=ca. 1 Hz), 2.64 and 3.63 (ABq, 2H, J=16 Hz), 5.43–5.9 (m, 2H), 6.77 (s, 1H) and 6.85–7.5 (m, 25H).

EXAMPLE 12

Diphenyl 1-(3-phenoxymethyl-7-oxo-4-thia-2,6-diazabicyclo(3,2,0)hept-2-en-6-yl)-1-(2,2,2-trichloroethoxycarbonyl)-prop-1-en-2-yl phosphate To a stirred solution of 2,2,2-trichloroethyl α-(3-phenoxymethyl-7-oxo-4-thia-2,6-diazabicyclo(3,2,0)hept-2-en-6-yl)-α-(1-hydroxyethylidene)acetate (2.33 g.) in tetrahydrofuran (30 ml.) under a nitrogen atmosphere at 20° C. was added triethylamine (0.74 ml.) followed by diphenylphosphoryl chloride (1.09 ml.). After stirring for 1.75 hours at 20° C., the reaction mixture was diluted with dichloromethane, washed with brine, dried with magnesium sulphate and evaporated to give the title compound as a pale yellow foam in essentially quantitative yield. TLC (silica) $R_f$ 0.63 (ethyl acetate). The product was a mixture of geometric isomers (ca. 3:1) about the enol phosphate double bond. NMR δ CDCl$_3$ 2.08 (d)+2.68 (d) (3H), 4.4–5.0 (m, 4H), 5.67–6.07 (m, 2H) and 6.63–7.43 (m, 15H).

EXAMPLE 13 p-Nitrobenzyl α-(3phenoxymethyl-7-oxo-4-thia-2,6-diazabicyclo(3,2,0)hept-2-en-6-yl)-α-(1-morpholinoethylidene)acetate To a stirred solution of 1-(3-phenoxymethyl-7-oxo-4-thia-2,6-diazabicyclo(3,2,0)hept-2-en-6-yl)-1-(p-nitrobenzyloxycarbonyl)-prop-1-en-2-yl diphenylphosphinate (1.34 g.) in tetrahydrofuran (20 ml.) at 0°–5° C. was added morpholine (0.38 ml.). After stirring for 6 hours at 0°–5° C., the solvent was evaporated and the residue dissolved in dichloromethane. The resulting solution was washed with water and then with saturated sodium chloride solution, dried with magnesium sulphate and evaporated to give the title compound as a pale yellow foam in essentially quantitative yield. The product obtained was a mixture of geometric isomers (ca. 1:1.4) about the enamine double bond and was identical to that produced in example 8.

EXAMPLE 14 p-Nitrobenzyl
α-(3-phenoxymethyl-7-oxo-4-thia-2,6-diazabicyclo(3,2,0)hept-2-en-6-yl)-α-(1-morpholinoethylidene)acetate To a stirred solution of phenyl 1-(3-phenoxymethyl-7-oxo-4-thia-2,6-diazabicyclo(3,2,0)hept-2-en-6-yl)-1-(p-nitrobenzyloxycarbonyl)-prop-1-en2-yl phenylphosphonate (1.37 g.) in tetrahydrofuran (20 ml.) at 0°–5° C. was added morpholine (0.383 ml.). After stirring for 3 hours at 0°–5° C., the solvent was evaporated and the residue dissolved in dichloromethane. The resulting solution was washed with water and then with saturated sodium chloride solution, dried with magnesium sulphate and evaporated to give the title compound as a pale yellow foam in essentially quantitative yield. The product obtained was a mixture of geometric isomers (ca. 1:1.4) about the enamine double bond and was identical to that produced in example 8.

EXAMPLE 15 p-Nitrobenzyl
α-(3-benzyl-7-oxo-4-thia-2,6-diazabicyclo(3,2,0)hept-2-en-6-yl)-α-(1-piperidinoethylidine)acetate To a stirred solution of p-nitrobenzyl α-(3-benzyl-7-oxo-4-thia-2,6-diazabicyclo(3,2,0)hept-2-en-6-yl)-α-(1-hydroxyethylidene)acetate (3.02 g.) in tetrahydrofuran (40 ml.) under a nitrogen atmosphere at 20° C. was added triethylamine (0.98 ml.) followed by diphenylphosphoryl chloride (1.45 ml.). After stirring for 2 hours, the reaction mixture was cooled to 0° C. and piperidine (0.76 ml.) was added. After stirring for 3 hours at 0°–5° C., the tetrahydrofuran was evaporated and the residue dissolved in dichloromethane. The resulting solution was washed with water and then with saturated sodium chloride solution, dried with magnesium sulphate and evaporated to give the title compound as a pale yellow foam in essentially quantitative yield. TLC (silica) $R_f$ 0.48 (dichloromethane-ethyl acetate 15:2). The product was a mixture of geometric isomers about the enol phosphate double bond. NMR δ CDCl$_3$ 1.13–1.77 (m, 6H), 1.67 (s)+2.33 (s) (3H), 2.9–3.4 (m, 4H), 3.83 (s, 2H), 5.15 (s, 2H), 5.55–5.93 (m, 2H), 7.25 (s, 5H) and 7.48 and 8.23 (ABq, 4H, J=9 Hz).

EXAMPLE 16

2,2,2-Trichloroethyl
α-(3-phenoxymethyl-7-oxo-4-thia-2,6-diazabicyclo(3,2,0)hept-2-en-6-yl)-α-(1-morpholinoethylidene)acetate To a stirred solution of 2,2,2-trichloroethyl α-(3-phenoxymethyl-7-oxo-4-thia-2,6-diazabicyclo(3,2,0)hept-2-en-6-yl)-α-(1-hydroxyethylidene) acetate (2.33 g.) in tetrahydrofuran (30 ml.) under a nitrogen atmosphere at 20° C. was added triethylamine (0.74 ml.) followed by diphenylphosphoryl chloride (1.09 (ml.) After stirring for 2 hours, the reaction mixture was cooled to 0° C. and morpholine (0.92 ml.) was added. After stirring for 2 hours at 0°–5° C., the tetrahydrofuran was evaporated and the residue dissolved in dichloromethane. The resulting solution was washed with water and then with saturated sodium chloride solution, dried with magnesium sulphate and evaporated to give the title compound as a pale yellow foam in essentially quantitative yield. TLC (silica) $R_f$ 0.20 (dichloromethane-ethyl acetate 15:2). The product was a mixture of geometric isomers (ca. 1.5:1) about the enol phosphate double bond. NMR δ CDCl$_3$ 1.83 (s)+2.37 (s) (3H), 3.0–3.9 (m, 8H), 4.48 and 4.92 (ABq, 2H, J=13 Hz), 4.93 (s, 2H), 5.75–6.10 (m, 2H) and 6.8–7.5 (m, 5H).

EXAMPLE 17 p-Nitrobenzyl
α-(3-phenoxymethyl-7-oxo-4-thia-2,6-diazabicyclo(3,2,0)hept-2-en-6-yl)-α-(1-morpholinoethylidene)acetate To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (4.69 g.) in tetrahydrofuran (60 ml.) under a nitrogen atmosphere at 0°–5° C. was added triethylamine (1.6 ml.) followed by dropwise addition of ethyl dichlorophosphate (1.36 ml.) over 5 minutes. After stirring for 3 hours at 20° C., the reaction mixture was cooled to 0° C. and morpholine (4.0 ml.) was added dropwise over 10 minutes with the reaction temperature maintained at 0°–5° C. After stirring for 3 hours at this temperature, the tetrahydrofuran was evaporated and the residue dissolved in dichloromethane. The resulting solution was washed with water and then with saturated sodium chloride solution, dried with magnesium sulphate and evaporated to give the title compound as a pale yellow foam in essentially quantitative yield. The product obtained was a mixture of geometric isomers (ca. 1:1.4) about the enamine double bond and was identical to that produced in example 8.

EXAMPLE 18 p-Nitrobenzyl
α-(3-phenoxymethyl-7-oxo-4-thia-2,6-diazabicyclo(3,2,0)hept-2-en-6-yl)-α-(1-morpholinoethylidene)acetate To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (4.69 g.) in tetrahydrofuran (60 ml.) under a nitrogen atmosphere at 0°–5° C. was added triethylamine (1.6 ml.) followed by dropwise addition of phenylphosphonic dichloride (1.63 ml.) over 5 minutes. After stirring for 3 hours at 20° C., the reaction mixture was cooled to 0° C. and morpholine (4.0 ml.) was added dropwise over 10 minutes with the reaction temperature maintained at 0°–5° C. After stirring for 3 hours at this temperature, the tetrahydrofuran was evaporated and the residue dissolved in dichloromethane. The resulting solution was washed with water and then with saturated sodium chloride solution, dried with magnesium sulphate and evaporated to give the title compound as a pale yellow foam in quantitative yield. The product obtained was a mixture of geometric isomers (ca. 1:1.4) about the enamine double bond and was identical to that produced in example 8.

EXAMPLE 19 p-Nitrobenzyl
α-(3-phenoxymethyl-7-oxo-4-thia-2,6-diazabicyclo(3,2,0)hept-2-en-6-yl)-α-(1-morpholinoethylidene)acetate To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (4.69 g.) in tetrahydrofuran (60 ml.) under a nitrogen atmosphere at 0°–5° C. was added triethylamine (1.6 ml.) followed by dropwise addition of phenyl dichlorophosphate (1.72 ml.) over 5 minutes. After stirring for 3 hours at 20° C., the reaction mixture was cooled to 0° C. and morpholine (4.0 ml.) was added dropwise over 10 minutes with the reaction temperature maintained at 0°–5° C. After stirring for 3 hours at this temperature, the tetrahydrofuran was evaporated and the residue dissolved in dichloromethane. The resulting solution was washed with water and then with saturated sodium chloride solution, dried with magnesium sulphate and evaporated to give the title compound as a yellow foam in essentially quantitative yield. The product obtained was a mixture of geometric isomers (ca. 1:1.4) about the enamine double bond and was identical to that produced in example 8.

EXAMPLE 20

Benzhydryl 7-phenylacetamido-3-hydroxy-3-cephem-4-carboxylate

To a stirred solution of benzhydryl α-(3-benzyl-7-oxo-4-thia-2,6-diazabicyclo(3,2,0)hept-2-en-6-yl)-α-(1-hydroxyethylidene)acetate (9.68 g.) in tetrahydrofuran (120 ml.) under a nitrogen atmosphere at 20° C. was added triethylamine (2.93 ml.) followed by diphenylphosphoryl chloride (4.35 ml.) After stirring for 3 hours, the reaction mixture was cooled to 5°–10° C., morpholine (3.75 ml.) was added and the mixture stirred for 2 hours at 5°–10° C. After cooling to −30° to −35° C., pyridine (1.62 ml.) was added followed by dropwise addition of bromine (1.00 ml.) over 10 minutes. The reaction mixture was stirred at −30° to −35° C. for 20 minutes and 5% hydrochloric acid (144 ml.) was added. After stirring at 20° C. for 1.5 hours the reaction mixture was extracted with ethyl acetate and the extract washed with water, dried with magnesium sulphate and evaporated to give a foam (10.3 g.) The foam (9.3 g.) was purified by column chromatography on silica gel (600 g.) with dichloromethane-acetone (20:1) as eluent to give 7.04 g. (78%) of the title compound as a foam. TLC (silica) $R_f$ 0.55 (ethyl acetate). NMR δ CDCl$_3$ 3.13 (s, 2H), 3.57 (s, 2H), 4.88 (d, 1H, J=4 Hz), 3.57 (dd, 1H, J=4 and 9 Hz) and 6.66–7.5 (m, 17H).

EXAMPLE 21 p-Nitrobenzyl 7-phenoxyacetamido-3-hydroxy-3-cephem-4-carboxylate

To a stirred solution of p-nitrobenzyl α-(3-phenoxymethyl-7-oxo-4-thia-2,6-diazabicyclo(3,2,0)hept-2-en-6-yl)-α-(1-hydroxyethylidene)acetate (9.38 g.) in tetrahydrofuran (120 ml.) under a nitrogen atmosphere at 20° C. was added triethylamine (3.21 ml.) followed by phenyl phenylphosphonochloridate (5.82 g.) After stirring for 2 hours at 20° C., the reaction mixture was cooled to 0° C. and morpholine (4.01 ml.) added. After stirring for 2.5 hours at 0°–5° C., the mixture was cooled to −30° to −35° C. and pyridine (1.62 ml.) added followed by dropwise addition of bromine (1.00 ml.) over a period of 10 minutes. The reaction mixture was stirred at −30° to −35° C. for 20 minutes and 5% hydrochloric acid (144 ml.) added. After stirring at 20° C. overnight the mixture was extracted with dichloromethane and the extracts washed with water and saturated sodium chloride solution, dried with magnesium sulphate and evaporated to dryness. The residue was dissolved in glacial acetic acid (10 ml.) and the resulting solution stirred for approximately 10 minutes to crystallise the product. The crystallisation was completed by addition of isopropanol (120 ml.) over 0.5 hour. The crystals were isolated by filtration, washed with isopropanol and dried in vacuo at 40° C. overnight. The yield of p-nitrobenzyl 7-phenoxyacetamido-3-hydroxy-3-cephem-4-carboxylate acetic acid solvate was 8.29 g. (76%).

EXAMPLE 22

4-Methoxybenzyl 7-phenoxyacetamido-3-hydroxy-3-cephem-4-carboxylate

To a stirred solution of 4-methoxybenzyl α-(3-phenoxymethyl-7-oxo-4-thia-2,6-diazabicyclo(3,2,0)hept-2-en-6-yl)-α-(1-hydroxyethylidene)acetate (4.54 g.) in tetrahydrofuran (60 ml.) under a nitrogen atmosphere at 0° C. was added triethylamine (1.6 ml.) followed by diphenylphosphoryl chloride (2.39 ml.) After stirring for 3 hours at 0°–5° C., morpholine (2.0 ml.) was added and the reaction mixture stirred for a further 3 hours at 0°–5° C. The mixture was cooled to −30° to −35° C. and pyridine (0.81 ml.) added followed by dropwise addition of bromine (0.5 ml.) over a period of 5 minutes. The reaction mixture was stirred at −30° to −35° C. for 20 minutes and 5% hydrochloric acid (72 ml.) added, followed by methanol (60 ml.) After stirring overnight at room temperature, the mixture was extracted with dichloromethane and the extract washed with water, dried with magnesium sulphate and evaporated. The residual gum was chromatographed on silica gel (300 g.) with dichloromethane-acetone (9:1) as eluent to give 3.6 g. (76.6%) 4-methoxybenzyl 7-phenoxyacetamido-3-hydroxy-3-cephem-4-carboxylate as a foam. TLC (silica) $R_f$ 0.5 (toluene-ethyl acetate 1:1). NMR δ CDCl$_3$ 2.53 (s, 2H), 3.73 (s, 3H), 4.47 (s, 2H), 4.93 (d, 1H, J=4 Hz), 5.13 (s, 2H), 5.50 (dd. 1H, J=4 and 9 Hz), 6.67–7.37 (m, 9H) and 7.53 (d, 1H, J=9 Hz).

EXAMPLE 23

2,2,2-Trichloroethyl 7-phenoxyacetamido-3-hydroxy-3-cephem-4-carboxylate

To a stirred solution of 2,2,2-trichloroethyl α-(3-phenoxymethyl-7-oxo-4-thia-2,6-diazabicyclo(3,2,0)hept-2-en-6-yl)-α-(1-hydroxyethylidene)acetate (2.33 g.) in tetrahydrofuran (30 ml.) under a nitrogen atmosphere at 20° C. was added triethylamine (0.74 ml.) followed by diphenylphosphoryl chloride (1.09 ml.) After stirring for 2 hours, the reaction mixture was cooled to 0° C., morpholine (0.92 ml.) was added and the reaction mixture stirred for 2 hours at 0°–5° C. The mixture was cooled to −30° to −35° C. and pyridine (0.42 ml.) added followed by the dropwise addition of bromine (0.25 ml.) over a period of 5 minutes. The reaction mixture was stirred at −30° to −35° for 20 minutes and 5% hydrochloric acid (60 ml.) added. After stirring for 2 hours at room temperature, the mixture was extracted with ethyl acetate and the extract washed with water, dried with magnesium sulphate and evaporated to give a yellow foam. The foam was purified by column chromatography on silica gel (100 g.) with dichloromethane-acetone (25:1) as eluent to give 1.8 g. (74.7%) 2,2,2-trichloroethyl 7-phenoxyacetamido-3-hydroxy-3-cephem-4-carboxylate as a foam. TLC (silica) $R_f$ 0.2 (toluene-ethyl acetate 1:1). NMR δ CDCl$_3$ 3.22 and 3.53 (ABq, 2H, J=18 Hz), 4.5 (s, 2H), 4.82 (s, 2H), 5.03 (d, 1H, J=4 Hz), 5.53 (dd, 1H, J=4 and 9 Hz), 6.7–7.37 (m, 5H) and 7.63 (d, 1H, J=9 Hz).

We claim:
1. A process for preparing an enamine of formula (IX):

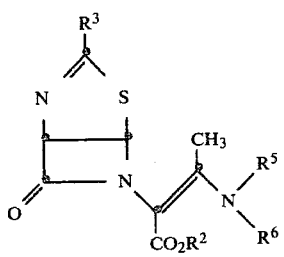

where $R^2$ is a carboxylic acid protecting group and $R^3$ is the residue of a carboxylic acid derived acyl group and where $R^5$ and $R^6$ are the same or different $C_{1-4}$ alkyl or $C_{7-10}$ aralkyl groups; or taken together with the ajacent nitrogen atom form a heterocyclic ring containing from 4 to 8 carbon atoms and optionally a further heteroatom selected from oxygen and nitrogen; by reacting an enol of formula (XI):

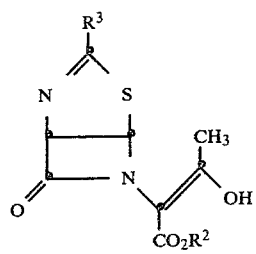

with a phosphorus reagent of formula (VII):

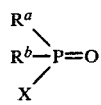

where $R^a$ and $R^b$ are the same or different and can each represent phenyl or phenoxy optionally substituted by one to three groups selected from $C_{1-4}$ alkyl, $C_{1-4}$ alkoxy, halogen and nitro; or is $C_{1-4}$ alkyl, $C_{1-4}$ alkoxy, $C_{3-8}$ cycloalkyl, $C_{3-8}$ cycloalkoxy, chlorine or bromine; X is chlorine, bromine, nitrile or azide; provided that:
(i) $R^a$ and $R^b$ cannot both be halogen; and
(ii) when X is nitrile or azide, $R^a$ and $R^b$ are the same or different phenoxy; $C_{3-8}$ cycloalkoxy or $C_{1-4}$ alkoxy groups, to form a product of formula (XII):

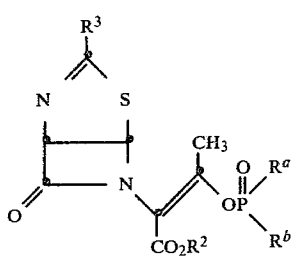

followed by reaction of this product with an amine of formula $HNR^5R^6$ to form the enamine of formula (IX).

2. The process according to claim 1, where a reagent of formula (VII) is utilized in which $R^a$ and $R^b$ are phenoxy optionally substituted by one to three groups selected from $C_{1-4}$ alkyl, $C_{1-4}$ alkoxy, halogen and nitro; $C_{1-4}$ alkoxy or $C_{3-8}$ cycloalkyloxy and X is bromine or chlorine.

3. A process according to claim 2, where $R^a$ and $R^b$ are phenoxy, $R^2$ is para-nitrobenzyl, $R^3$ is benzyl or phenoxymethyl, $R^5$ and $R^6$ taken together with the adjacent nitrogen atom represent a morpholino group and X is chlorine.

4. In the process for preparing a 3-hydroxy-cephalosporin of formula (VIII):

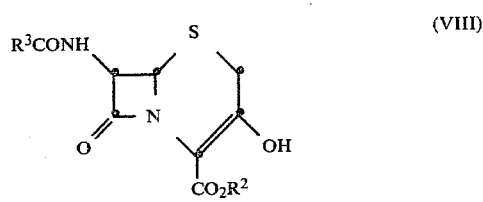

where $R^2$ and $R^3$ are as defined in claims 1, 2, or 3 which process comprises:
(a) halogenating a compound of formula (IX) as defined in claim 1, and
(b) cyclising the halo product (X):

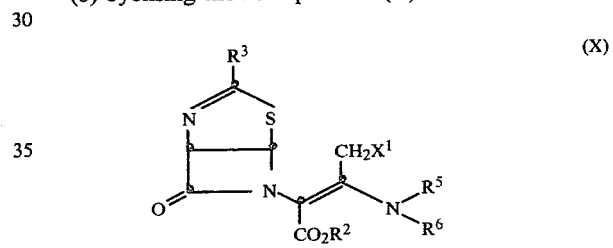

where $X^1$ is chlorine, bromine or iodine, into the 3-hydroxy cephalosporin of formula (VIII), the improvement which comprises preparing the compound of the formula (IX) by the process of claim 1.

5. A process according to claim 4, wherein the halogenation in step (a) is effected with molecular bromine.

6. A process for preparing an enamine of formula (IX) as defined in claim 1 which comprises reacting a compound of formula (XII) as defined in claim 1 with an amine of formula $HNR^5R^6$.

7. A compound of formula (XII):

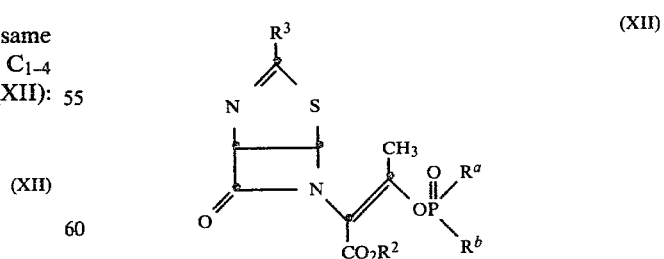

where $R^2$, $R^3$, $R^a$ and $R^b$ are as defined in claim 1 in either (E)- or (Z)-form.

8. A compound of formula (XII) as claimed in claim 7 wherein $R^a$ and $R^b$ are phenoxy, $R^2$ is p-nitrobenzyl and $R^3$ is benzyl or phenoxymethyl.

* * * * *